United States Patent
Mitchell

(10) Patent No.: US 11,845,029 B2
(45) Date of Patent: Dec. 19, 2023

(54) SCENT PRESENTATION SYSTEM AND METHOD OF USE

(71) Applicant: Jeffrey R. Mitchell, University City, MO (US)

(72) Inventor: Jeffrey R. Mitchell, University City, MO (US)

(*) Notice: Subject to any disclaimer, the term of this patent is extended or adjusted under 35 U.S.C. 154(b) by 0 days.

(21) Appl. No.: 17/691,113

(22) Filed: Mar. 9, 2022

(65) Prior Publication Data

US 2022/0288516 A1 Sep. 15, 2022

Related U.S. Application Data

(60) Provisional application No. 63/158,865, filed on Mar. 9, 2021.

(51) Int. Cl.
*B01D 45/08* (2006.01)
*B01D 45/02* (2006.01)

(52) U.S. Cl.
CPC ............. *B01D 45/02* (2013.01); *B01D 45/08* (2013.01)

(58) Field of Classification Search
CPC ........ B01D 45/02; B01D 45/08; A01K 15/02; A61L 9/122
See application file for complete search history.

(56) References Cited

U.S. PATENT DOCUMENTS

| | | | | |
|---|---|---|---|---|
| 2,058,044 A | * | 10/1936 | Spencer | B01D 21/0066 210/538 |
| 3,747,347 A | * | 7/1973 | Ciraolo | F01N 1/083 60/309 |
| 4,011,157 A | * | 3/1977 | Pennebaker, Jr. | B41J 2/195 95/287 |
| 5,149,347 A | * | 9/1992 | Turner | B01D 45/08 96/136 |
| 6,193,774 B1 | * | 2/2001 | Durdag | B01D 45/08 55/385.6 |
| 6,419,730 B1 | * | 7/2002 | Chavez | B01D 45/08 55/433 |
| 6,478,461 B1 | * | 11/2002 | Frank | B01D 53/261 34/135 |
| 7,785,400 B1 | * | 8/2010 | Worley | B01D 45/12 96/155 |
| 7,914,595 B2 | * | 3/2011 | Nakamura | F27B 9/3005 55/482 |

(Continued)

*Primary Examiner* — Dung H Bui
(74) *Attorney, Agent, or Firm* — David E. Crawford; Crawford I.P. Law

(57) ABSTRACT

A scent presentation system for segregating a desired scent from other scents suspended in a gas. The desired scent has a density that differs from that of another scent in the gas. The system includes a housing having a sloping top wall and a pair of elongated sloping side walls extending downward from the top wall on opposite sides of the top wall. The top wall and the pair of side walls define a channel extending between an upstream end and a downstream end of the housing. The system has a separating gate extending downward into the channel from the top wall to a lower end positioned inside the channel. The gate separates the channel into upstream and downstream chambers. The upstream end has an inlet port allowing the gas to enter the channel, and the downstream end has an outlet port allowing the gas to exit the channel.

12 Claims, 1 Drawing Sheet

(56) References Cited

U.S. PATENT DOCUMENTS

| | | | |
|---|---|---|---|
| 8,308,959 B2* | 11/2012 | Noles, Jr. | B01D 21/0045 96/182 |
| 11,285,405 B2* | 3/2022 | Johnson | B01D 17/0217 |
| 2014/0109533 A1* | 4/2014 | Horiuchi | F01M 13/04 55/464 |
| 2015/0090122 A1* | 4/2015 | Hemstock | B01D 45/02 96/197 |
| 2019/0083918 A1* | 3/2019 | Nakata | B01D 47/06 |

* cited by examiner

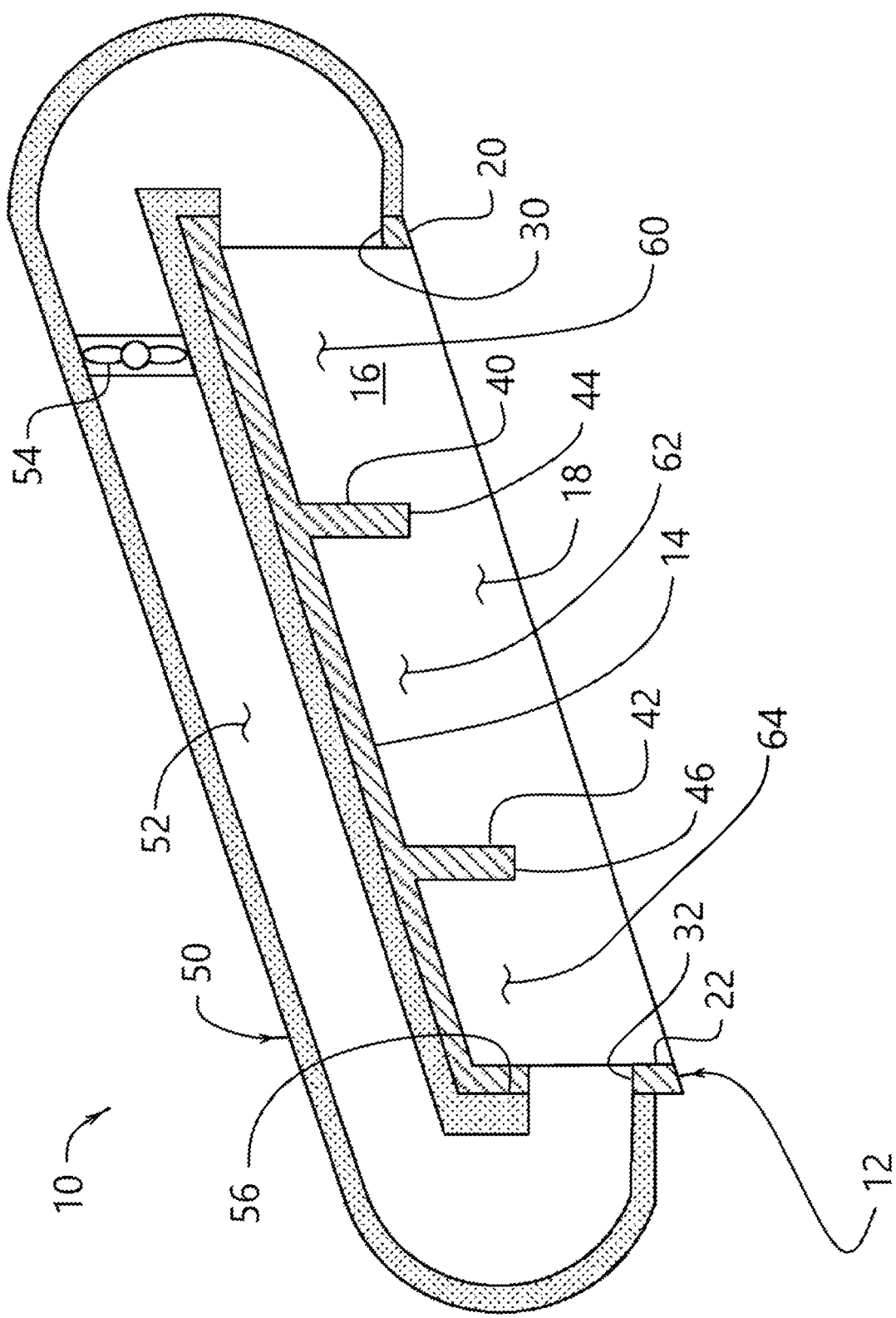

SCENT PRESENTATION SYSTEM AND METHOD OF USE

CROSS-REFERENCE TO RELATED APPLICATIONS

The present application claims priority to U.S. Provisional Patent Application 63/158,865 filed Mar. 9, 2021, which is hereby incorporated by reference in its entirety.

BACKGROUND

The present disclosure generally relates to methods and devices for presenting odors to a sentient being, and more specifically, to a system for segregating a particular scent and presenting the segregating scent to a being such as a canine or dog.

Some common systems for storing an odor comprises a sealed enclosure containing gas (e.g., air) including a scent. To present the scent to a dog, the enclosure is opened and positioned in the vicinity of the dog so the dog can be exposed to the scent and learn to identify the scent. For example, the scent of a particular drug may be stored in a sealed enclosure for use when training a dog to identify trace amounts of the drug in a vehicle. Other common systems comprise a sealed enclosure containing an absorbent scented swab. The absorbent swab is exposed to the scent to collect the scent and the swab is stored in the sealed enclosure after scent collection. To present the scent to a dog, the swab is removed from the enclosure and introduced to the dog for examination. As an example, a swab may be used to collect a scent of an explosive for use when training a dog to identify trace amounts of the explosive on traveler's luggage or clothing.

One of the problems associated with these common scent storage systems is that the scent may acquire the smell of its environs. For example, the odor of chemicals used to make the enclosure may mix during storage contaminating the desired scent with other odors. Additionally, long term storage increases the likelihood that the scent will be contaminated during storage so that the stored scent can no longer be used for training a dog to recognize a particular scent. Therefore, these common systems usually have a limited useful lifespan.

Another problem associated with these common systems is that some scents present hazards to the dog. For example, scents produced by a disease could infect a dog, resulting in its illness or death, rendering any scent recognition training useless. Because the cost of producing a well-trained dog typically is quite high, the possibility of infecting a dog, causing illness or death, and resulting in need for an expensive replacement is financially undesirable. Thus, protecting dogs from hazardous scents during training is important.

Although developments have been made in odor or scent storage systems, there remains a need for further improvement.

BRIEF SUMMARY

In one aspect, the present disclosure includes a scent presentation system for segregating a desired scent from a plurality of scents suspended in a gas. The desired scent has a density that differs from that of another scent in the plurality of scents. The scent presentation system comprises a housing having an elongated sloping top wall extending downward from an upstream end of the housing to a downstream end of the housing opposite the upstream end. The housing includes a pair of elongated sloping side walls extending downward from the elongated sloping top wall between the upstream end of the housing and the downstream end of the housing on opposite sides of the top wall. The top wall and the pair of side walls defining a channel extending between the upstream end of the housing and the downstream end of the housing. The system also comprises a separating gate extending downward into the channel from the top wall to a lower end positioned inside the channel. The separating gate separates the channel into an upstream chamber and a downstream chamber. The upstream end of the housing has an inlet port allowing the gas to enter the channel at the upstream end of the housing. The downstream end of the housing has an outlet port allowing the gas to exit the channel at the downstream end of the housing.

BRIEF DESCRIPTION OF THE DRAWINGS

FIG. 1 is a schematic cross section of an exemplary scent retention and presentation system described herein.

DETAILED DESCRIPTION

Referring now to the drawings and in particular to FIG. 1, a system for retaining or storing a scent and presenting the scent to a dog is designated in its entirety by the reference number 10. The system 10 includes a main presentation housing, generally designated by 12, having an elongated sloping top wall 14 and opposite elongated sloping side walls 16 (only one of which is visible in FIG. 1) defining a channel 18 extending between a higher upstream end 20 of the housing and a lower downstream end 22 of the housing that is opposite the upstream end. The upstream end 20 of the housing 12 has an inlet port 30 allowing gas (e.g., air) to enter the channel 14 at the upstream end of the housing. Further, the downstream end 22 of the housing 12 has an outlet port 32, allowing gas to exit the channel 14 at the downstream end of the housing.

As also shown in FIG. 1, separation gates or barriers 40, 42 are provided at selected longitudinal positions along the channel 14. In the illustrated example, each of the gates 40, 42 has a height that is equal to the other gates. Because the top wall 14 slopes downward from the higher upstream end 20 of the housing 12 to the lower downstream end 22 and the gates 40, 42 have equal heights, the elevation of the lower ends 44, 46 of the gates are different from each other.

As further illustrated in FIG. 1, the system 10 includes a recirculation duct, generally designated by 50, providing a return passage 52 extending between the outlet port 32 and the inlet port 30 of the housing to carry gas exiting the channel 14 through the outlet port to the inlet port. As a result, recirculating duct 50 recirculates gas exiting the channel 14 to the inlet port 30. The recirculation duct 50 includes a recess that is sized and shaped for receiving the main presentation housing 12 as shown. Further, a fan 54 provided inside the recirculation duct 50 is selectively operable for driving gas exiting the outlet port 32 through the return passage 52 to the inlet port 30. As also shown in FIG. 1, the duct 50 includes a recess 56 that is sized and shaped for receiving the housing 12 and aligning the return passage 52 with the outlet port 32 and the inlet port 30

As will be appreciated, different scents have different densities such that a group of scents held in a volume of gas tend to stratify such that a heavier or denser scent tends to sink or fall in the volume of gas and a lighter or less dense scent tends to float or rise in the volume of gas. The system 10 takes advantage of this stratification phenomenon to separate scents so the scent presented to the dog consists primarily of the desired scent and not mixed with other scents. When the fan 54 is energized to push gas containing a plurality of scents along the channel 14, a less dense scent amongst the plurality of scents in the gas will be captured upstream from the upstream gate 40. A heavier or denser scent amongst the plurality of scents will pass under the lower end 44 of the upstream gate 40 and will be captured upstream from the downstream gate 42. A scent that is heavier still will pass under the lower end 46 of the downstream gate 42. Thus, the scents contained in the gas may be separated into chambers 60, 62, 64 formed in part by the gates 40, 42.

As will be appreciated, the desired separated scent may be withdrawn from the corresponding chamber and presented to the dog. Further, the system 10 permits the dog to be exposed to a gas containing a stronger and more precise scent profile.

Although the specification includes examples, the disclosure's scope is indicated by the following claims. Furthermore, although the specification has been described in language specific to structural features and/or methodological acts, the claims are not limited to the features or acts described above. Rather, the specific features and acts described above are disclosed as examples for embodiments of the disclosure.

As various changes could be made in the above constructions without departing from the scope of the invention, all matter contained in the above description or shown in the accompanying drawings shall be interpreted as illustrative and not in a limiting sense.

Insofar as the description above and the accompanying drawing disclose any additional subject matter that is not within the scope of the claims below, the disclosures are not dedicated to the public and the right to file one or more applications to claims such additional disclosures is reserved.

When introducing elements in this description, the articles "a", "an", "the", and "said" are intended to mean that there are one or more of the elements. The terms "comprising", "including", and "having" are intended to be inclusive and mean that there may be additional elements other than the listed elements.

What is claimed is:

1. A scent presentation system for segregating a desired scent from a plurality of scents suspended in a gas, the desired scent having a density that differs from that of another scent in the plurality of scents, said scent presentation system comprising:
    a housing having an elongated sloping top wall extending downward from an upstream end of the housing to a downstream end of the housing opposite the upstream end, said housing including a pair of elongated sloping side walls extending downward from the elongated sloping top wall between the upstream end of the housing and the downstream end of the housing on opposite sides of the top wall, the top wall and the pair of side walls defining a channel extending between the upstream end of the housing and the downstream end of the housing;
    a separating gate extending downward into the channel from the top wall to a lower end positioned inside the channel, said separating gate separating the channel into an upstream chamber and a downstream chamber;
    a recirculation duct operatively connected to the housing and defining a return passage extending between the outlet port and the inlet port;
    a fan positioning along the return passage for recirculating gas exiting the channel through the outlet port to the inlet port;
    wherein:
        the upstream chamber includes at least portion positioned at an elevation higher than the downstream chamber;
        the upstream end of the housing has an inlet port allowing the gas to enter the channel at the upstream end of the housing;
        the downstream end of the housing has an outlet port allowing the gas to exit the channel at the downstream end of the housing
        the recirculation duct has a recess sized and shaped for receiving the housing;
        the return passage provides fluid communication between the output port and the inlet port separate from the channel; and
        the housing is selectively removable from the recess.

2. A scent presentation system as recited in claim 1, wherein:
    said separating gate is a first separating gate extending downward into the channel from the top wall to a first lower end positioned inside the channel, said first separating gate separating the channel into a first upstream chamber and a first downstream chamber; and
    said scent presentation system further comprises a second separating gate extending downward into the channel from the top wall to a second lower end positioned inside the channel, said second separating gate separating the channel into a second upstream chamber and a second downstream chamber.

3. A scent presentation system as recited in claim 2, wherein the second upstream chamber includes at least portion positioned at an elevation higher than the second downstream chamber.

4. A scent presentation system as recited in claim 2, wherein the first lower end is positioned at level higher than the second lower end.

5. A scent presentation system as recited in claim 2, wherein the first downstream chamber comprises the second upstream chamber.

6. A scent presentation system as recited in claim 2, wherein the second upstream chamber consists of the first downstream chamber.

7. A scent presentation system as recited in claim 1, wherein the separating gate has a vertical upstream face.

8. A scent presentation system as recited in claim 1, wherein at least one of the upstream chamber and the downstream chamber is adapted to remove a separated scent sample therefrom.

9. A scent presentation system for segregating a desired scent from a plurality of scents suspended in a gas, the desired scent having a density that differs from that of another scent in the plurality of scents, said scent presentation system comprising:
    a housing having an elongated top wall sloping downward from an upper end having an inlet port allowing gas to enter the channel to a lower end having an outlet port allowing gas to exit the channel;
    a separating gate extending downward into the channel from the top wall to a lower end inside the channel, said separating gate separating the channel into an upstream chamber and a downstream chamber, the upstream chamber having at least a portion that is higher than the separating gate;

a recirculation duct having a recess adapted to receive the housing therein, said recirculation duct having a return passage adapted to direct gas exiting the channel through the outlet port to enter the channel through the inlet port; and a fan positioned in the return passage for moving gas through the return passage toward the inlet port;

wherein:

the recirculation duct has a recess sized and shaped for receiving the housing;

the return passage provides fluid communication between the output port and the inlet port separate from the channel; and the housing is selectively removable from the recess.

10. A scent presentation system as recited in claim 9, wherein at least one of the upstream chamber and the downstream chamber is adapted to remove a separated scent sample therefrom.

11. A scent presentation system as recited in claim 9, wherein:

said separating gate is a first separating gate extending downward into the channel from the top wall to a first lower end positioned inside the channel, said first separating gate separating the channel into a first upstream chamber and a first downstream chamber; and said scent presentation system further comprises a plurality of separating gates including said first separating gate, each separating gate of said plurality of separating gates extending downward into the channel from the top wall to a second lower end positioned inside the channel into a corresponding upstream chamber and a corresponding downstream chamber.

12. A scent presentation system as recited in claim 9, wherein the separating gate has a vertical upstream face.

\* \* \* \* \*